United States Patent [19]

Weissman

[11] Patent Number: 4,616,999
[45] Date of Patent: Oct. 14, 1986

[54] BONDING DENTAL PIN
[75] Inventor: Bernard Weissman, New York, N.Y.
[73] Assignee: IPCO Corporation, White Plains, N.Y.
[21] Appl. No.: 742,429
[22] Filed: Jun. 7, 1985
[51] Int. Cl.⁴ .............................................. A61C 5/04
[52] U.S. Cl. .................................................. 433/225
[58] Field of Search ....................... 433/225, 220, 174

[56] References Cited
U.S. PATENT DOCUMENTS 759,498  5/1904  Bosch ................................... 433/225
4,449,937  5/1984  Weissman ............................ 433/225

Primary Examiner—Robert Peshock
Attorney, Agent, or Firm—Goodman & Teitelbaum

[57] ABSTRACT

A bonding dental pin for aiding in the retention of a thin layer of bonding material onto a tooth structure, the bonding dental pin including a lower anchoring portion for securement into the tooth structure. A coaxial cylindrical neck portion of the pin is embedded into the bonding material, and an upper manipulating portion of the pin is available for securing the anchoring portion into the tooth structure. A first stop flange is interposed between the anchoring and neck portions, and a second head portion flange is interposed between the neck and manipulating portions. The confronting surfaces of the flanges are respectively concave to define a pocket therebetween for aiding in maintaining the bonding material around the neck portion.

23 Claims, 7 Drawing Figures

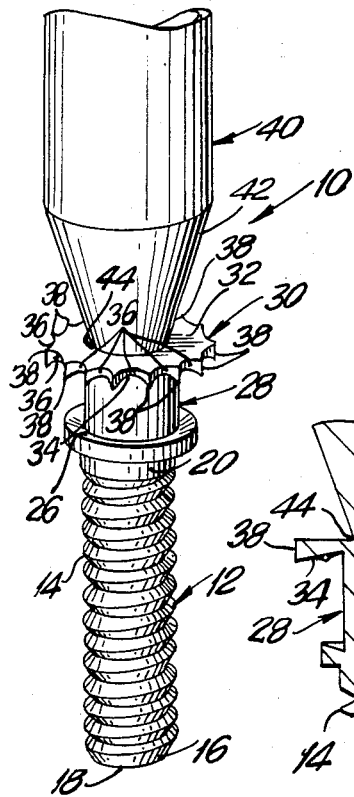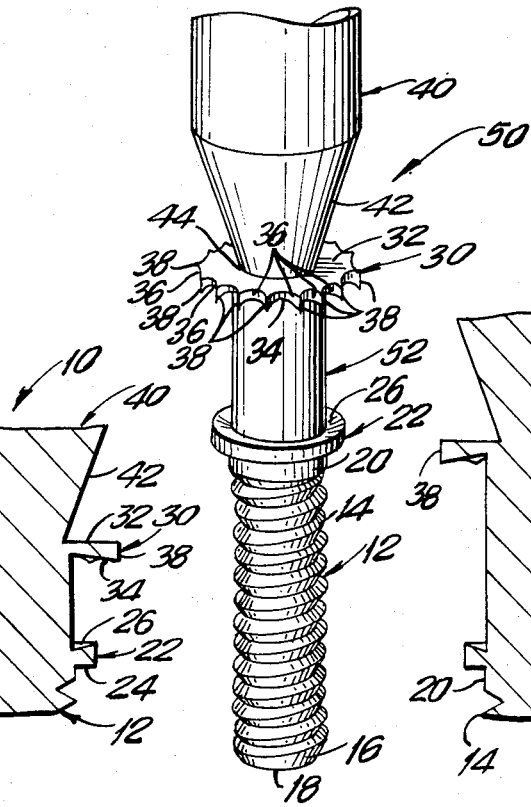
FIG.1  FIG.2  FIG.3  FIG.4
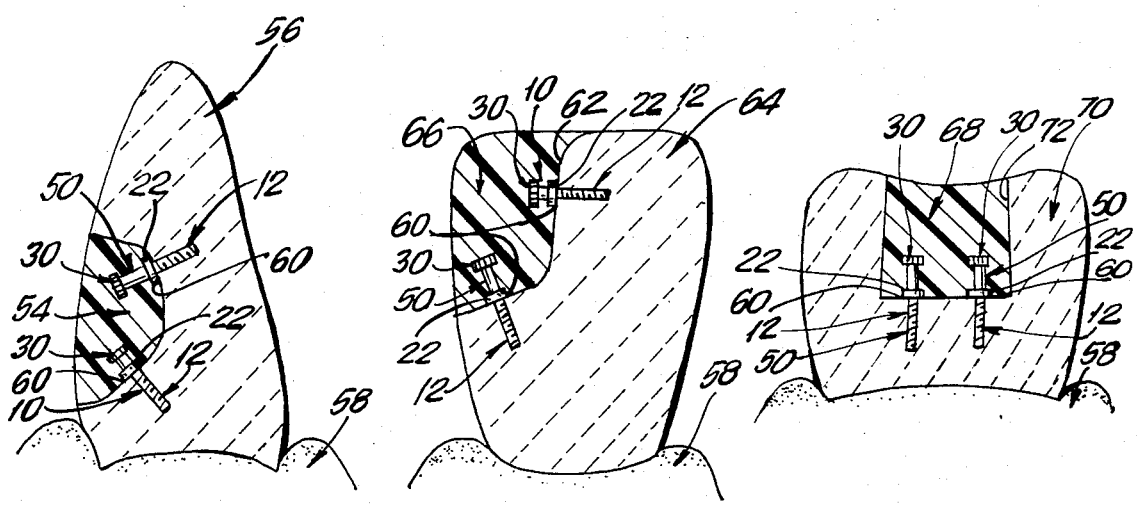
FIG.5  FIG.6  FIG.7

BONDING DENTAL PIN

BACKGROUND OF THE INVENTION

This invention relates to dental techniques, and more particularly, to a dental pin for use in retaining a bonding layer onto a tooth being repaired.

Dental pins are well known for use in retaining a superstructure built upon a dental understructure of a tooth. The tooth is cut down to prepare the understructure, a number of channels are formed into the understructure, and dental pins are inserted into the channels. The dental superstructure is then built up onto the understructure using standard dental techniques, being secured onto the understructure by the dental pins which aid in the retention of the superstructure onto the tooth stub. By way of example, one such dental anchor is described in my U.S. Pat. No. 4,449,937 which shows the use of an anchoring portion having a frustroconical depth limiting collar for restricting the insertion depth of the anchoring portion into the tooth understructure. A non-circular coaxial retaining portion extends from the anchoring portion which is embedded within the tooth superstructure. A manipulating portion is frangibly connected to the retaining portion and snaps off, by the limiting action of the collar, after the anchoring portion is seated into the tooth understructure.

Although superstructures are built up when the dentition is generally broken away or decayed so as to require the damaged tooth to be cut down so that only a tooth stub remains, other types of dental repairs are now known where it is not necessary to build up an entire superstructure. For example, bonding material is typically utilized to provide a thin layer on a portion of the tooth structure which may be damaged, chipped, or the like. The bonding material is used to fill in the crack or chip in the tooth structure, being retained directly onto the tooth enamel or structure.

While the use of bonding material has been found quite effective, the bonding material has a tendency of loosening from the tooth structure since it is only retained in place by means of the bonding nature of the material itself.

The typical prior art dental pins or dental anchors utilized for retaining superstructures are not at all suited for use with such bonding material since the pins or anchors are excessively large with respect to the thin bonding layer and the particular pin or anchor structure is not suited for use with the bonding material.

Accordingly, there is required a dental pin or anchor which can be utilized for aiding in retaining a thin bonding layer onto a tooth structure.

SUMMARY OF THE INVENTION

Accordingly, it is an object of the present invention to provide a bonding dental pin or anchor which can be utilized to retain a thin bonding layer onto a tooth structure.

Another object of the present invention is to provide a bonding dental pin or anchor which is sufficiently small in size for use in retaining a thin bonding layer onto a tooth structure.

Yet a further object of the present invention is to provide a bonding dental pin or anchor including a retention portion which can be embedded into the thin bonding layer and can be securely held within the bonding layer even though the bonding layer is of small size.

Yet a further object of the present invention is to provide a bonding dental pin or anchor including an anchoring portion which can be secured into the tooth structure, the anchoring position including an improved retention mechanism for securement within a thin bonding layer to aid in the retention of the bonding layer onto the tooth structure.

Another object of the present invention is to provide a method of retaining a thin bonding layer onto a tooth structure through the use of a bonding dental pin or anchor.

Briefly, there is provided a bonding dental pin or anchor for aiding in the retention of a thin bonding layer onto a tooth structure. The dental pin or anchor includes an elongated cylindrical member having a lower threaded body portion which can be secured into the tooth structure. A coaxial cylindrical neck portion extends from the threaded body portion. The neck portion is embedded into the bonding layer. A coaxial cylindrical head portion extends from the neck portion and is available for use in manipulating the dental pin or anchor while securing the lower threaded body portion into the tooth structure.

A first radially projecting flange is interposed between the body portion and the neck portion, and serves to limit the insertion of the body portion into the tooth structure. A second radially projecting flange defines the head portion, being interposed between the neck portion and a manipulating portion. The second flange aides in embedding the dental pin within the bonding layer to help in the retention thereof onto the tooth structure. A frangible reduced diameter throat portion at the juncture of the manipulating portion with the head portion permits easy severing of the manipulating portion after the body portion is secured in the tooth structure.

In order to aid in embedding the dental pin or anchor within the thin bonding material, the confronting faces of the first and second flanges are respectively concave in order to define a pocket therebetween. In this manner, even though the bonding dental pin or anchor is of substantially small size, it provides adequate retention within the bonding material to insure that the bonding layer is retained in place onto the tooth structure. Furthermore, the second flange of the head portion is knurled in a scallop-type arrangement.

BRIEF DESCRIPTION OF THE DRAWINGS

With the above and additional objects and advantages in view, as will hereinafter appear, this invention comprises the devices, combinations and arrangements of parts hereinafter described by way of example, and illustrated in the accompanying drawings of a preferred embodiment in which:

FIG. 1 is a perspective view of one embodiment of the bonding dental pin in accordance with the present invention;

FIG. 2 is an enlarged fragmented cross sectional view of the central portion of the bonding dental pin of FIG. 1, showing the interconnection of the neck portion with the upper manipulating portion and the lower anchoring portion;

FIG. 3 is a perspective view similar to that shown in FIG. 1 of another embodiment of the bonding dental pin having an elongated neck portion;

FIG. 4 is an enlarged fragmented cross sectional view similar to that shown in FIG. 2, showing the elongated neck portion; and FIGS. 5, 6 and 7 show cross sectional views of tooth structures having bonding dental pins of the present invention inserted therein for retaining various bonding layers in place on the tooth structures.

In the various figures of the drawings, like reference characters designate like parts.

DETAILED DESCRIPTION OF THE PREFERRED EMBODIMENTS

Referring now to the drawings, FIGS. 1 and 2 show a first embodiment of a bonding dental pin or anchor 10, in accordance with the present invention. The dental pin 10 is of a substantially cylindrical nature and includes a lower anchoring portion 12 having a peripheral thread 14 formed thereabout and terminating in a chambered tip 16 having a substantially flat distal end 18. The upper end of the thread 14 terminates in a substantially smooth cylindrical portion 20 above which there is provided a radially outwardly extending circular flange 22. The lower surface 24 of the flange 22 is substantially flat. However, the upper surface 26 is concave directed downwardly into the flange 22.

Coaxial with the anchoring portion 12 and having a substantially similar diameter to the cylindrical portion 20, is a substantially smooth cylindrical neck portion 28 disposed on the upper surface 26 of the flange 22. At the upper end of the neck portion 28, there is again provided a radially outwardly projecting circular flange 30 defining a head portion, the top surface 32 of which is substantially flat and the lower surface 34 being concave directed upwardly into the flange 30. The upper and lower concave surfaces 34, 26 confront each other and define therebetween a pocket, as will hereinafter be described. The outer peripheral edge of the upper radial flange 30 is knurled in a scallop-type arrangement to provide a plurality of circular cutouts 36 and spaced apart projecting thin ridges providing vertically extending pointed fins 38. The head portion flange 30 has a larger diameter than the lower flange 22.

At the upper end of the bonding dental pin 10, there is provided a manipulating portion 40 having a periphery larger than the neck portion 28 the diameter of the manipulating portion 40 being about equal to the diameter of the head portion flange 30. The lower end of the manipulating portion 40 integrally continues into an inwardly tapered frustroconical portion 42 which joins the top surface 32 of the head portion flange 30. The juncture between the frustroconical portion 42 and the top surface 32 provides a reduced diameter frangible throat portion 44.

FIGS. 3 and 4 show a substantially identical bonding pin or anchor 50, wherein the only difference is that the neck portion 52 of the pin 50 has a greater length than the neck portion 28 of the pin 10 shown in FIGS. 1 and 2. The use of the greater neck portion 52 permits varying the size of the bonding dental pin to accommodate the amount of bonding material in which the pin must be embedded. The remaining portions of the pin 50 shown in FIGS. 3 and 4 are identically identified the same as those portions of the pin 10 shown in FIGS. 1 and 2.

As can best be seen in FIG. 5 by way of example, the use of the bonding dental pin of the present invention facilitates the securing a thin bonding layer 54 onto a tooth structure 56 situated within a gum area 58. The tooth structure 56 has a lateral chip therein which requires repairing or patching. Normally, the bonding material or layer 54 would be directly placed onto the tooth structure to smooth out the peripheral surface of the tooth structure 56 in such a manner as to substantially match the existing enamel of the tooth. However, the use of such bonding material or layer 54 alone on the tooth structure relies essentially upon the bonding capabilities of the bonding material or layer 54 which is somewhat limited as to the thickness of the layer applied. The bonding material or layer would therefore have a tendency of loosening or falling off from the tooth structure when applied too thick, even though the bonding layer is relatively thin when compared to the tooth structure. The present bonding dental pins aid in the retention of the bonding layer 54 onto the tooth structure 56. Specifically, there is shown a smaller neck portion type of bonding dental pin 10, of the type described in FIGS. 1 and 2, as well as the use of a larger neck portion type of bonding dental pin 50 of the type described in FIGS. 3 and 4. In each case, the lower anchoring portion 12 is inserted into the tooth structure 56 by rotating the manipulating portion 40. Such insertion can be achieved by directly threading the anchor portion into the tooth structure. Alternately, channels can be initially formed into the tooth structure by using a standard dental tool such as a dental drill. Each channel is formed of an adequate depth to receive one of the bonding dental pins. One dental pin is then inserted into each channel until its flange portion 22 reaches the outer surface of the tooth structure. The surface upon which the flange portion 22 rests, should be flat, as is shown by the flattened portion 60 beneath the flange portion 22.

The neck portion 28 or 52 of the bonding dental pin 10 or 50 will project beyond the anchoring portion 12. When the dental pin is properly seated in the tooth structure, the manipulating portion 40 can be snapped off. The bonding dental pin itself can be inserted by means of a dental tool well known in the dental art, which grasps onto the manipulating portion 40 for threading the bonding dental pin into the tooth structure. The frangible throat portion 44 can be of a size so that as soon as the bonding dental pin is threaded into the channel, and the limiting flange 22 reaches the outer surface of the tooth structure, the frangible throat portion 44 will automatically snap off from the head portion flange 30 thus removing the manipulating portion 40 from the remaining seated portion of the dental pin.

The bonding material or layer 54 is then applied to repair or patch the damaged area of the tooth, being suitably contoured at its periphery to match the periphery of the tooth structure 56 itself. The bonding material will fill the portion around the neck portion of the pin with the upper flange portion being retained in place within the bonding layer 54. The use of both the knurled periphery including the vertically extending pointed fins 38 and the enlarged upper flange 30 aid in the retention capability of the bonding dental pin. Similarly, by making the confronting surfaces 26, 34 of the flanges concave, a pocket is defined therebetween for retaining bonding material so as to also aid in keeping the bonding material around the neck portion, and thereby insuring that the bonding dental pin will be properly embedded within the bonding layer 54.

As shown in FIG. 6, the bonding dental pins can be used at various locations in securing bonding material to the tooth structure. FIG. 6 shows an edge chip 62 formed in the tooth structure 64 with the bonding material or layer 66 providing a repair or patch at the corner of the tooth. The larger neck portion pin 50 and a smaller neck portion pin 10 are again utilized to secure the bonding material or layer 66 onto the tooth structure 64.

FIG. 7 shows a bonding layer 68 in the occlusal surface of a tooth 70. A substantially U-shaped channel 72 is cut out in order to receive the bonding material 68. Two longer neck portion types of bonding dental pins 50 are utilized for retaining the bonding layer 68 in place. Obviously, any combination of the dental pins 10 and 50 can be used to retain the bonding layer in place.

The size of the bonding dental pins 10 and 50 are extremely small. By way of example, the threaded anchoring portion 12 can be 0.020 inches in diameter and 0.062 inches in length. The neck length for the neck portion 28 shown in FIG. 1 is 0.012 inches and that of the neck portion 52 shown in FIG. 3 is 0.027 inches. The entire length of each pin 10 and 50, including the manipulating portion 40, can be 0.355 inches. The diameter of the smaller lower flange 22 is 0.026 inches and that of the larger head portion flange 30 is 0.032 inches. Thus, as indicated above, the length of the neck portion 28, 52 in both cases is less than one half the length of the anchoring portion 12 to accommodate the thin layer of bonding material, both neck portions 12, 52 having the same diameter as the anchoring portion 12.

It should be appreciated, that in order to maintain a fixed over all length for both of the bonding pins, so that the length of the bonding pins 10 and 50 can be maintained constant regardless of the lengths of their neck portions in the bonding pin 50 with the longer neck portion, the manipulating portion 40 thereof would be reduced in size relative to the manipulating portion of pin 10 in order to maintain a fixed length for the pins 10 and 50.

As can be appreciated, with such small neck portions 28 and 52, retention of the neck portions in the bonding material would normally not be adequate. However, by use of the confronting concave surfaces on the facing flange portions, as well as by using the enlarged upper flange with the knurled pointed pin-like outer edge, the retention capabilities of the small pins 10 and 50 are improved so that even though the length is extremely small, the retention capability provided by the bonding dental pins 10 and 50 is great enough to maintain a bonding layer secured onto the tooth structure. Typically, the bonding dental pin can be fabricated from a precious metal material or any other suitable material well known in the dental art.

Numerous alterations of the structure herein disclosed will suggest themselves to those skilled in the art. However, it is to be understood that the present disclosure relates to a preferred embodiment of the invention which is for purposes of illustration only and is not to be construed as a limitation of the present invention.

What is claimed is:

1. A bonding dental pin for aiding in retention of a thin layer of bonding material onto a tooth structure, comprising:
    an elongated body member;
    a lower body portion of said body member including anchoring means for securing said lower body portion into the tooth structure;
    said body member including a neck portion for embedding in the bonding material;
    a radially projecting stop flange interposed between said lower body portion and said neck portion for limiting insertion depth of said body portion into the tooth structure;
    a radially projecting head portion flange disposed at an upper end of said neck portion and longitudinally spaced from said stop flange for embedding in the bonding material;
    retention means for securing an upper body portion of said body member within the bonding material; and
    said retention means including providing said head portion flange with an inwardly directed concave lower surface and said stop flange with an inwardly directed concave upper surface, said concave lower and upper surfaces confronting each other to define a pocket therebetween for receiving the bonding material therein.

2. A bonding dental pin as in claim 1, wherein said retention means includes said head portion flange having a larger diameter than said stop flange for securement within the bonding material.

3. A bonding dental pin as in claim 2, wherein said head portion flange has a diameter of approximately 0.032 inches and said stop flange has a diameter of approximately 0.026 inches.

4. A bonding dental pin as in claim 3, wherein said lower body portion has a longitudinal length of approximately 0.062 inches and a diameter of approximately 0.020 inches.

5. A bonding dental pin as in claim 4, wherein said neck portion is cylindrical and has a longitudinal length of approximately 0.012 inches and a diameter approximately equal to said diameter of said lower body portion.

6. A bonding dental pin as in claim 4, wherein said neck portion is cylindrical and has a longitudinal length approximately equal to said diameter of said lower body portion.

7. A bonding dental pin as in claim 1, wherein an outer peripherial edge of said head portion flange is knurled in a scallop-type arrangement to provide a plurality of spaced apart vertically extending thin pointed fins.

8. A bonding dental pin as in claim 1, wherein a manipulating member is connected to an upper surface of said head portion flange for securing said anchoring means into the tooth structure, said manipulating member including a frangible reduced diameter throat portion adjacent to said head portion flange to permit severing of said manipulating member after said stop flange is seated on the tooth structure.

9. A bonding dental pin as in claim 8, wherein said body member and said manipulating member have a combined longitudinal length of approximately 0.355 inches.

10. A bonding dental pin as in claim 9, wherein said neck portion has a longitudinal length of approximately 0.012 inches.

11. A bonding dental pin as in claim 9, wherein said neck portion has a longitudinal length of approximately 0.027 inches.

12. A bonding dental pin as in claim 1, wherein said neck portion has a longitudinal length less than one half of entire longitudinal length of said lower body portion for accommodating the thin layer of bonding material.

13. A bonding dental pin for aiding in retention of a thin layer of bonding material onto a tooth structure, comprising:
    an elongated body member;

a lower body portion of said body member including anchoring means for securing said lower body portion into the tooth structure;

said body member including a neck portion for embedding in the bonding material;

a radially projecting stop flange interposed between said lower body portion and said neck portion for limiting insertion depth of said body portion into the tooth structure;

a radially projecting head portion flange disposed at an upper end of said neck portion and longitudinally spaced from said stop flange for embedding in the bonding material;

retention means for securing an upper body portion of said body member within the bonding material; and said retention means including providing an outer peripheral edge of said head portion flange with a knurl in a scallop-type arrangement to provide a plurality of spaced apart vertically extending thin pointed fins.

14. A bonding dental pin as in claim 13, wherein said neck portion has a longitudinal length less than one half of entire longitudinal length of said lower body portion for accommodating the thin layer of bonding material.

15. A bonding dental pin as in claim 13, wherein said retention means includes said head portion flange having a larger diameter than said stop flange for securement within the bonding material.

16. A bonding dental pin as in claim 15, wherein said head portion flange has a diameter of approximately 0.032 inches and said stop flange has a diameter of approximately 0.026 inches.

17. A bonding dental pin as in claim 16, wherein said lower body portion has a longitudinal length of approximately 0.062 inches and a diameter of approximately 0.020 inches.

18. A bonding dental pin as in claim 17, wherein said neck portion is cylindrical and has a longitudinal length of approximately 0.012 inches and a diameter approximately equal to said diameter of said lower body portion.

19. A bonding dental pin as in claim 17, wherein said neck portion is cylindrical and has a longitudinal length approximately equal to said diameter of said lower body portion.

20. A bonding dental pin as in claim 13, wherein a manipulating member is connected to an upper surface of said head portion flange for securing said anchoring means into the tooth structure, said manipulating member includes a frangible reduced diameter throat portion adjacent to said head portion flange to permit severing of said manipulating member after said stop flange is seated on the tooth structure.

21. A bonding dental pin as in claim 20, wherein said body member and said manipulating member have a combined longitudinal length of approximately 0.355 inches.

22. A bonding dental pin as in claim 21, wherein said neck portion has a longitudinal length of approximately 0.012 inches.

23. A bonding dental pin as in claim 21, wherein said neck portion has a longitudinal length of approximately 0.027 inches.

* * * * *